US006847740B1

(12) United States Patent
Birkle

(10) Patent No.: US 6,847,740 B1
(45) Date of Patent: Jan. 25, 2005

(54) METHOD FOR THE OPTICAL DETECTION OF OBJECTS, WHOSE SURFACES CAN REFLECT OR SCATTER LIGHT AND WHICH HAVE SELF-AFFINE, OR SELF-SIMILAR, OR FRACTAL PATTERNS OR STRUCTURES

(76) Inventor: Gebhard Birkle, Stiegerstrasse 21, 78337 Öhningen (DE)

( * ) Notice: Subject to any disclaimer, the term of this patent is extended or adjusted under 35 U.S.C. 154(b) by 0 days.

(21) Appl. No.: 09/566,553

(22) Filed: May 8, 2000

Related U.S. Application Data

(63) Continuation of application No. 09/196,295, filed on Nov. 19, 1998, now abandoned, which is a continuation of application No. 08/640,943, filed as application No. PCT/DE94/01321 on Nov. 10, 1994, now abandoned.

(30) Foreign Application Priority Data

Nov. 10, 1993 (DE) .......................................... 43 38 307

(51) Int. Cl.⁷ ................................................. G06K 9/36
(52) U.S. Cl. ...................................... 382/276; 382/249
(58) Field of Search ........................ 382/210–211, 249, 382/276, 286, 108; 359/15, 107; 702/11

(56) References Cited

U.S. PATENT DOCUMENTS 4,628,468 A * 12/1986 Thompson et al. ........... 702/12
4,789,933 A * 12/1988 Chen et al. .................. 382/128
4,914,461 A * 4/1990 Hori .............................. 396/62
5,077,640 A * 12/1991 Butler, Jr. ..................... 362/11
5,132,831 A * 7/1992 Shih et al. ................... 359/107

* cited by examiner

Primary Examiner—Daniel Mariam
(74) Attorney, Agent, or Firm—Horst M. Kasper

(57) ABSTRACT

The invention relates to a method for the optical detection of objects or object streams, wherein the surfaces of the objects or object streams are capable of reflecting or of scattering light, and wherein the objects or object streams can exhibit or form or generate self-affine or self-similar or fractal patterns or structures on the surfaces or in themselves, by employing an illuminating device for illuminating the objects or object streams and an optical imaging and receiving device with a following electronic evaluation for receiving and evaluating the imaging light reflected or scattered by the surfaces. The imaging ray bundle is scanned as a sequence of light patterns, wherein a similitude-transformation algorithm forms the basis of the scanning such that the connection of the individual light patterns relative to each other spatially and/or timely is a scaling or rotation or translation of self-affine or self-similar or fractal, and wherein at least two variables are set up. A storing and actualization of the detection events, resulting from the scanning over the variables, in the form of value pairs, is performed within a memory storage in each one step of the scaling or rotation or translation. The calculation of the scaling or rotation or translation function (for example, in case of a based scaling, the value pairs result in a linear function in case of the presence of a self-similarity of the objects or object streams) is performed by way of the logarithm over the variables of the scaling or rotation or translation.

19 Claims, 6 Drawing Sheets

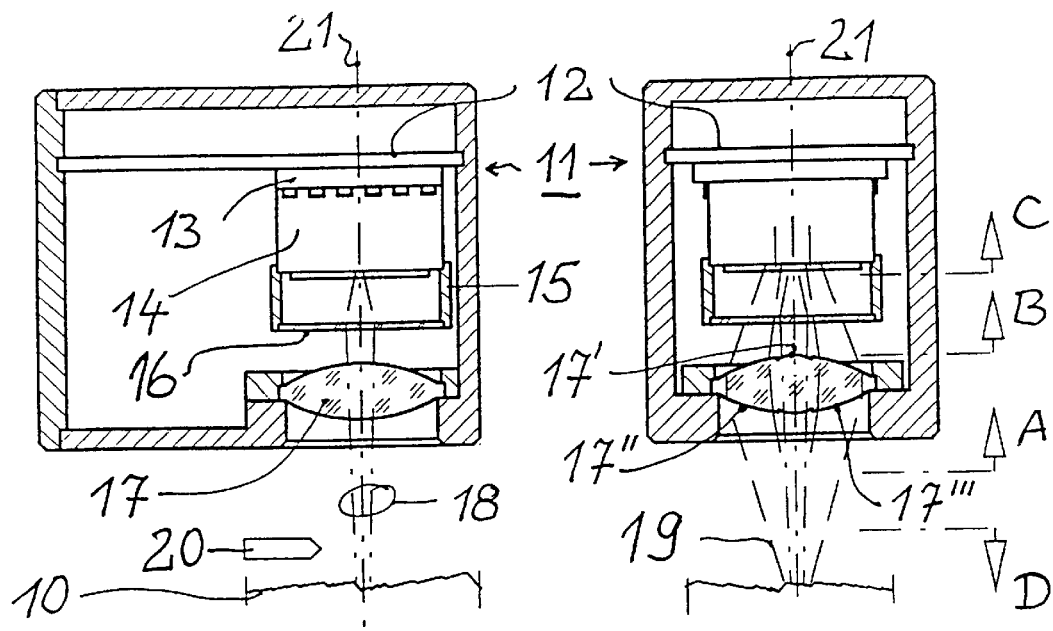
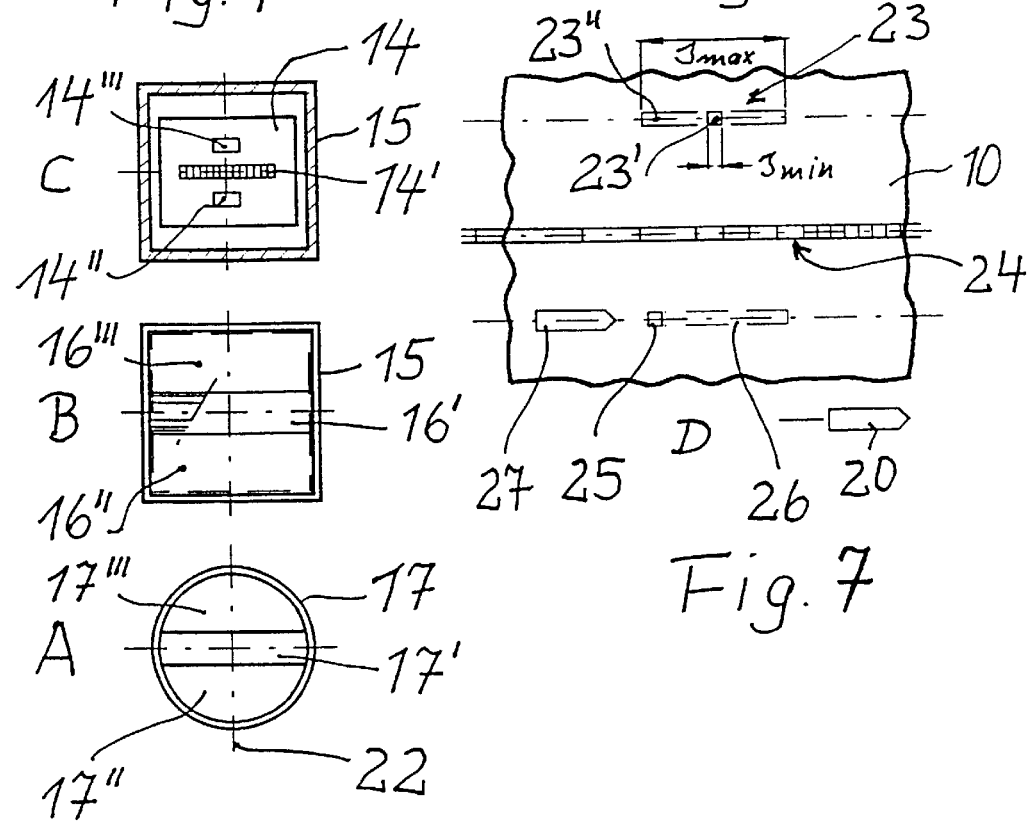

METHOD FOR THE OPTICAL DETECTION OF OBJECTS, WHOSE SURFACES CAN REFLECT OR SCATTER LIGHT AND WHICH HAVE SELF-AFFINE, OR SELF-SIMILAR, OR FRACTAL PATTERNS OR STRUCTURES

CROSS-REFERENCES TO RELATED APPLICATIONS

This is a continuation application filed based on application Ser. No. 09/196,295, filed Nov. 19, 1998, now abandoned, which in turn is a continuation application of parent application Ser. No. 08/640,943, filed May 6, 1996, now abandoned which is a 371 of PCT/DE94/01321 Jan. 10, 1994.

STATEMENT REGARDING FEDERALLY SPONSORED RESEARCH OR DEVELOPMENT

Not relevant

REFERENCE OF A "MICROFICHE APPENDIX" (SEE 37 CFR 1.96)

Not relevant

BACKGROUND OF THE INVENTION

1. Field of the Invention

The invention relates to a method for the optical detection of objects or object streams, such as resting objects or moving object streams, wherein their surfaces are capable of reflecting or scattering light, and which objects can exhibit, or can form, or can generate self-affine or self-similar or fractal patterns or structures on the surfaces or in themselves according to the preamble of claim 1.

2. Description of the Related Art Including Information Disclosed Under 37 CFR 1.97 and 1.98.

Self-similar or self-affine or fractal formations or structures are testimonies of an omnipresent structure type, represented in the surrounding objects and the processes in the nature. The Koch curve or the Sierpinski triangle are cited as classic self-similar or, respectively, fractal formations in geometric-mathematical representation. A structure is designated as exactly self-similar if it can be subdivided into arbitrarily small parts, of which each part is a small copy of the complete structure, whereby it is important that the small parts are generated from the complete structure by a similitude transformation. Two objects are in this situation similar if they exhibit, disregarding their size, the same shape; transformations between the objects, where the transformations include connections of scalings, rotations, and translations, are in this case similitude transformations.

Natural self-affine structures appear less ideally in the environment; they are more or less stochastically modulated and in particular the defining property of the invariance to scaling is often limited to certain size ranges of the structure-forming features, in this case one calls the situation to be self-affine to self-similar. Similarly, several different self-affine or fractal structures can appear superposed as multifractals. The fractal dimension or self-similar dimension (FD) is employed, among others, as measurement size or characteristic size both for the mathematical-ideal fractals as well as for natural fractals, wherein the fractal dimension or self-similar dimension (FD) appears as a rational number and is a measurement of the degree of the complexity of the connections or, respectively, the width of variation of two values, wherein the self-similar dimension FD follows a low of exponentiation.

A measurement-technical use of the self-similar dimension has up to now hardly found any application in the quality control and the process control. In fact, the self-affinity or, respectively, fractals appear in many natural patterns, however in a variety of phenotypes, which are viewed as measurement-technically impeding the measurement, such that the evaluation of fracture faces, of pore patterns or of scar patterns, of bubbles in foams, of folding patterns, or of wetting faces can in most cases only be performed according to the appearance to the eye. In principle, such a capturing by way of a picture data processing with a video camera and a storage medium would be possible, however in connection with a very specific system adaptation and thus, at the end, an uninteresting relationship between costs and use value. Furthermore, an overirradiation of the feature by secondary light in case of connected images of surfaces generates also an information loss for a subsequent picture data processing by way of a video camera. For this purpose, the fracture faces or textures, which are frequently carriers of self-affine patterns to self-similar patterns, are very much subject to interference.

A device for the large-area optical topography measurement for investigating diffuse-reflecting surfaces by way of projected patterns on the object surfaces has become known from the German Printed Patent document DE-U1-9301901. Furthermore, a method for the measurement of the roughness of the surface of work pieces has become known from the German Printed Patent document DE-A1-3532690, wherein the surface of irradiated with light and the distribution of the intensity of the reflected light is measured with a converter and the signal of roughness is calculated therefrom. Furthermore, it is known from P. Pfeifer "Fractal Dimension as Working Tool for Surface-Roughness Problems" in Applications of Surface Science 18, 1984, pp. 146–164, Amsterdam, that the fractal dimension can be employed for determining the roughness of surfaces.

BRIEF SUMMARY OF THE INVENTION

Object of the Invention

It is an object of the invention to monitor, to capture or, respectively, to evaluate by way of optical means the surfaces of objects or of object streams, such as resting objects or moving object streams, i.e. also courses of processes, in order to be able, based on the optical capture of patterns or structures, to make statements relative to the quality or properties of the object or of the stream of objects or, respectively, the course of the processes, as long as such objects or object streams exhibit self-affinity or self-similitude or fractals in the investigated region. The invention is also based on the purpose to allow a determination of the speed of the relative motion of a moved object relative to the imaging device and to the receiving device.

Disclosure of the Invention and its Advantages

The solution of the object comprises according to the invention that a) the imaging ray bundle is scanned as a sequence of light patterns, wherein a similitude-transformation algorithm forms the basis of the scanning in such a way that the connection of the individual light patterns to each other spatially and/or timely is a scaling or rotation or translation of self-affine or self-similar or fractal and that at least two variables are set up, b) a storage and actualization of the detection events, resulting from the scanning over the variables, in the form of value pairs, is performed within a memory storage in each one of the steps of the scaling or rotation or translation, c) the calculation of the scaling function or the rotation function or the translation function (for example, the value pairs result in a linear function upon presence of self-similitude of the objects of object streams in case a scaling forms the basis) occurs over the variables of the scaling or rotation or translation by way of their logarithm.

A device for the performing of the method is characterized by a) an optical device, which is capable of scanning the imaging ray bundle as a sequence of light patterns, wherein a similitude-transformation algorithm is the basis of the scanning such that the connection of the individual light patterns to each other spatially and/or timely is a scaling or rotation or translation of self-affine or self-similar or fractal, and wherein at least two variables are set up, b) there occurs a storage and actualization of the detection events, resulting from the scanning over the variables, in the way of value pairs within a memory storage within each one of the steps of the scaling or rotation or translation, c) the calculation of the scaling function or the rotation function or the translation function (for example, the value pairs result in a linear function upon presence of self-similitude of the objects or object streams in case a scaling forms the basis) occurs over the variables of the scaling or rotation or translation by way of their logarithm. Further advantageous embodiments of the inventions are characterized in the remaining subclaims.

In an advantageous way, the illuminating ray bundle can also be modulated with a sequence of light patterns, wherein a similitude-transformation algorithm forms the basis of the modulation such that the connection of the individual light patterns to each other spatially or timely is a scaling or rotation of translation of self-affine or self-similar or fractal, and where at least two variables are set up, wherein the modulation of the illuminating ray bundle, the scanning of the imaging ray bundle, as well as the control of the storage for receiving the value pairs are tuned to each other in a controlled way by way of a control.

In connection with the scanning of the imaging ray bundle and/or the modulation of the illuminating ray bundle, it is preferred that the light patterns of the generated sequences are scaled and comprise a group of illuminating faces (light pattern elements), which form a scaling of self-affine or exactly self-similar or fractal light patterns in the plane with respect to at least one common property, namely spatially and/or timely, when a self-affine or exactly self-similar or fractal pattern or a self-affine or exactly self-similar or fractal structure is to be recognized as a constant. The number of memory channels formed is the same as the number of variables selected or, respectively, present. Further advantageous embodiments of the invention are characterized in the subclaims.

The invention is associated with the advantage that processes can be monitored or patterns or structures can be recognized with the invention method in order to determine the underlying, self-similar process or the underlying object, which carries the respective self-similar pattern or the respective self-similar structure. It is a precondition that the process or the object exhibits self-similitude or, respectively, self-affinity or is a fractal, because self-similar or, respectively, fractal structures are indicators for the processes generating them. Since self-affinity occurs in many processes and natural patterns, a determination of the process or, respectively, of the object is possible such that, based on the method which generates as it were an expected image, there is available an industrial practical testing or a process control with a fractal dimension (FD) determination by way of which the fracture faces, pore patterns and scar patterns, folding patterns, or wetting faces, or bubble formations in foams and liquids can be monitored and monitored according to the expected image. The core of the invention comprises to illuminate and to activate objects or object streams by way of self-affine or self-similar up to fractal structured light patterns and to determine thereby the fractal-dimension (FD) function of the object for detection of self-affine, self-similar or fractal patterns or structures of objects or object streams.

The terms "scaling," "rotation," and "translation" are understood as mathematical terms. In the following, a similitude-transformation algorithm is mainly a scaling, wherein in the same way rotation or translation functions can form the basis of similitude-transformation algorithm.

In case of a scaling, for example, elements of varying size are counted in a test pattern according to at least one parameter, for example the size, wherein at least two variables are forming the basis of the different size, where the variables can be in the x-y plane or in the x-y plane and the time axis or in the x plane or in the y plane and the time axis; this means that the parameter or the variable "size" is scaled or normalized. Value pairs can be recorded as a result, where the value pairs allow a statement relative to the frequency or the covering density of the differently sized elements relative to a grid (standard grid value). In case of only one single scanning point, the activation pattern or, respectively, points can also only be disposed on the time axis.

Thus, the scaling operations, or the rotation operations, or translation operations are performed in an advantageous way on the sensor side, i.e. on the side of the illumination and imaging, wherefor, one is independent relative to the image size and one needs only a reduced data volume relative to a video processing.

In order to obtain an optimum selectivity in the detection of optical superpositions of pattern elements and of object features, in certain cases it can be advantageous to structure the activation and receiving side, for example, in order to avoid an overirradiation at fracture faces, in a general way in order to suppress interferences. Certain scaling parameters can require such a channel-forming mutual arrangement, for example, in the scaling through polarization degrees or a discoloration scale (crystal discolorations upon water intercalation in the crystal grid).

The searched-for arrangements of features are in most cases random structures, which can require a computational consideration depending on the scaling properties with respect to the more or less perfect covering of the pattern elements and object features. The counting of feature overlappings with scaled grid faces, determination of the box dimension is not affected in this regard.

BRIEF DESCRIPTION OF THE SEVERAL VIEWS OF THE DRAWINGS

Short Description of the drawing, where there is shown in.

DETAILED DESCRIPTION OF THE INVENTION

Figure 1:
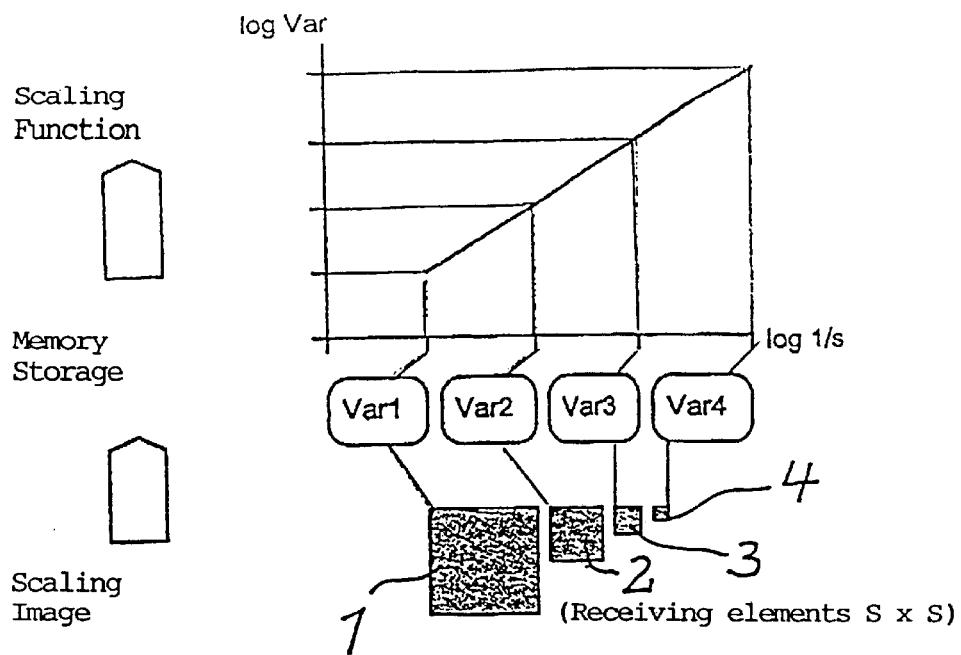
FIG. 1 an illustration of the principle of the method.
Figure 3:
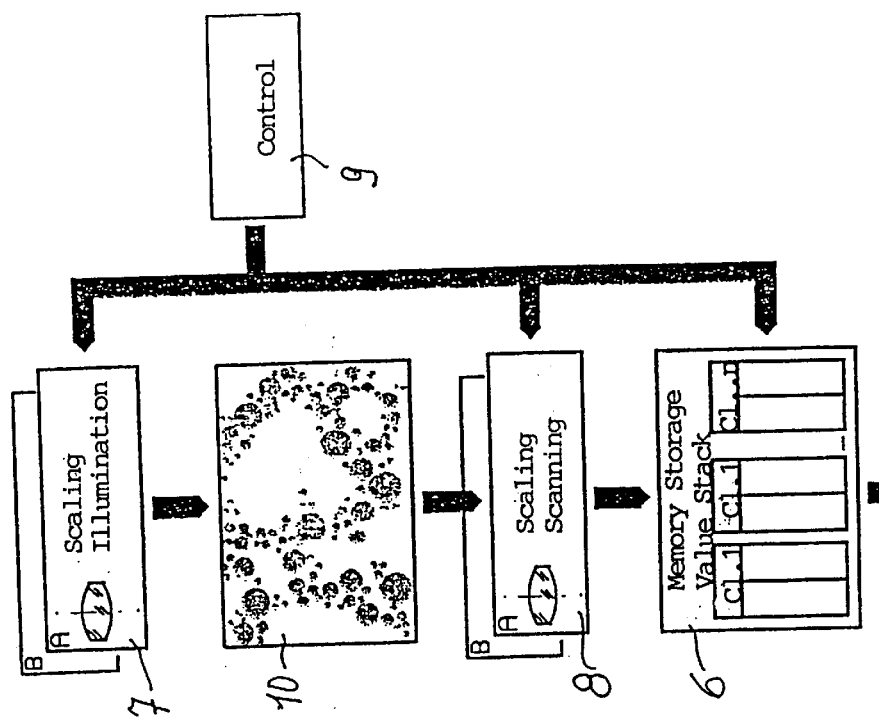
Figure 2:
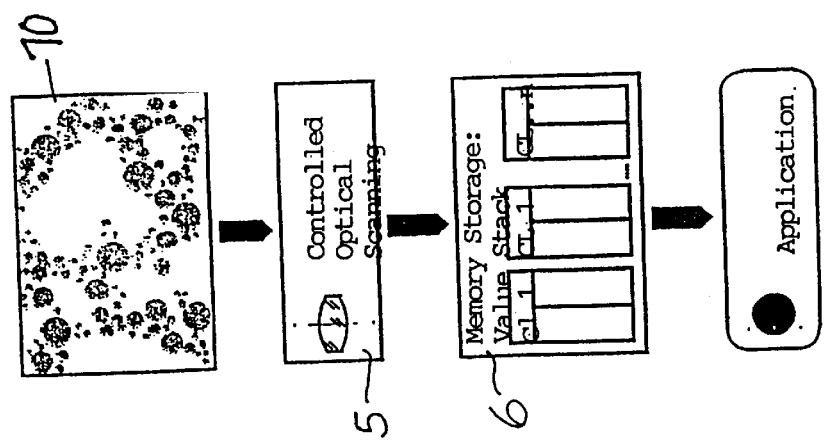
FIG. 2 a principle representation of a structure-specific receiving system and evaluation system, where the imaging ray bundle is controlled relative to the algorithm and is optically scanned, FIG. 3 a further principle representation of a structure-specific receiving system and evaluation system, where the imaging ray bundle is controlled relative to the algorithm and is optically scanned, FIG. 4 a section through a device for the sequential generation of light patterns for illumination, FIG. 5 a view of FIG. 4 rotated by 90 degrees, FIGS. 6 A, B, C partial views corresponding to the sections "A," "B," "C" in FIG. 5, FIG. 7 a partial view of "D" in FIG. 5, FIG. 8 a longitudinal section (A—A) through a further device for the sequential generation of illuminating light patterns, FIG. 9 a section along the line B—B in FIG. 8, FIG. 10 an example of a linear illuminating light pattern, FIG. 11 an example of a circular illuminating light pattern, FIG. 12 a construction variation relative to the device of FIG. 8, FIG. 13 the respective configuration of object, illuminating pattern, emitter and receiving elements in unfolded representation, FIG. 14 a longitudinal section through a construction variant for a face-covering or two-dimensional scanning with a comparatively broad scanning track, FIG. 15 a section along the line B—B in FIG. 15, FIGS. 16a, b, c, d a drawn-apart representation of the illumination, of the object surface, of the receiving element array, as well as of the example of the resulting scanning grid, and FIG. 17 a further principle representation of the method.
Figure 8:
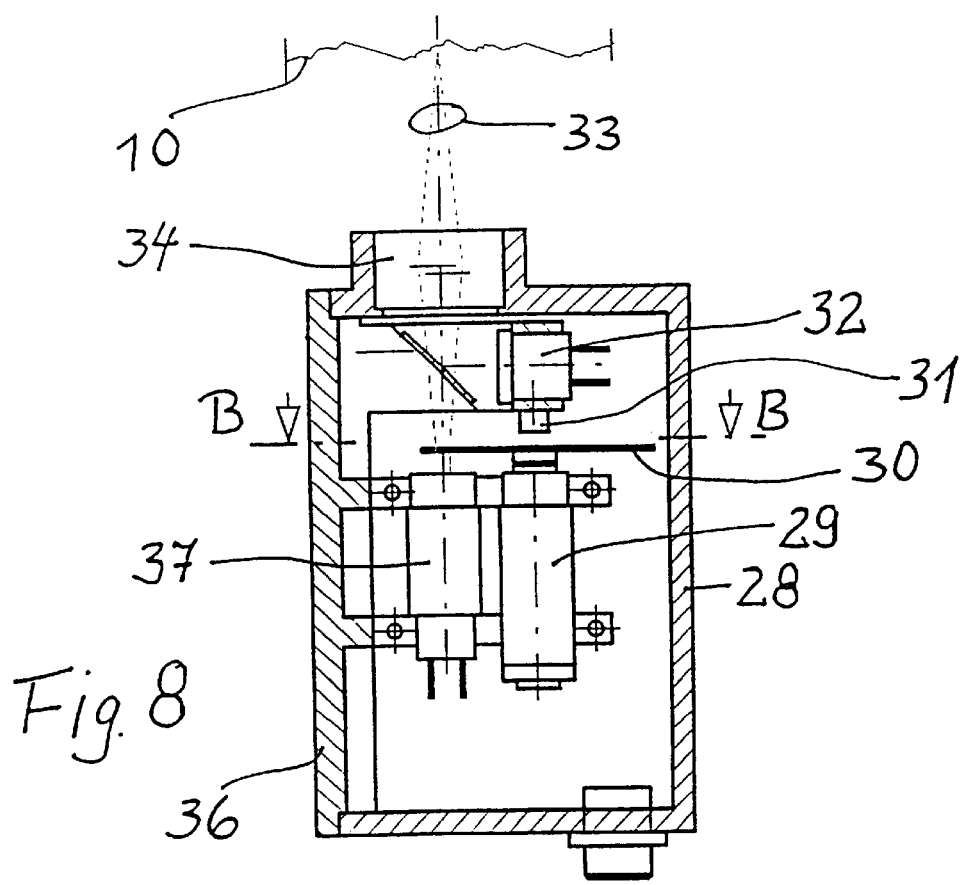
Figure 9:
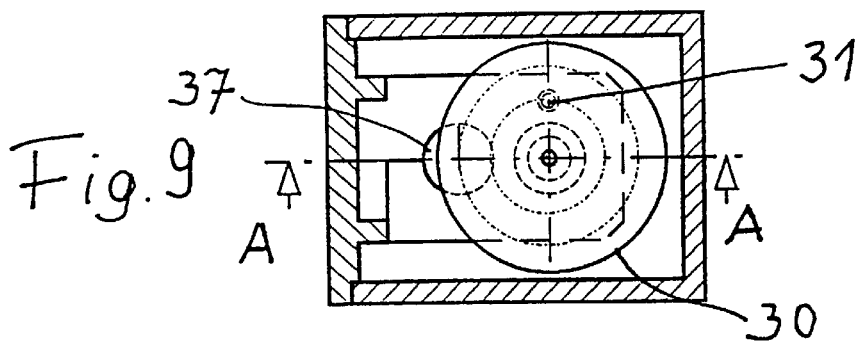

The principle method is illustrated by way of FIGS. 1 through 3. An object 10 or, respectively, an object surface is illuminated by way of a light source, wherein, in case of simply positioned detections, either only the illuminating ray bundle (FIGS. 1 and 2), or in case of a more complex situation, the imaging light bundle and the illuminating ray bundle (FIG. 3) are scanned or illuminated and scanned with reference to an algorithm as a sequence of light patterns for the detection of class-specific contrasts of the object 10. The connection of the individual light patterns to each other occurs spatially and/or timely as a scaling of self-affine or self-similar to fractal. For example, four variables $Var_1$, $Var_2$, $Var_3$, $Var_4$ are established in FIG. 1, which correspond to the differently sized light patterns and which are in this case differently sized square receiving elements 1, 2, 3, 4, S×S, wherein the sizes S×S of the receiving elements are mutually connected based on the selected similitude-transformation algorithm. Within a memory storage there is performed a storage and actualization of the detection results, resulting from the scanning over the variables, by way of value pairs within each step of the scaling. The calculation of the scaling function is performed by way of the logarithm of the scaling over the variables of the scaling, wherein the value pairs, in case of an underlying self-affinity of the searched-for patterns or structures of the object or of the object stream, result in a linear function, i.e. the searched-for scaling function. This function means the plotting of the term $\log(Var_n)$ over the term $\log(1/S)$ upon normalization or, respectively, the plotting of the term $\log(S)$. It is essential that a logarithmization is performed not on the calculator side or on the software side, but that the logarithmization inherent in the method results based on the similitude-transformation algorithm and from the fact that the searched-for patterns or structures are self-similar or self-affine or fractal.

Figure 17:
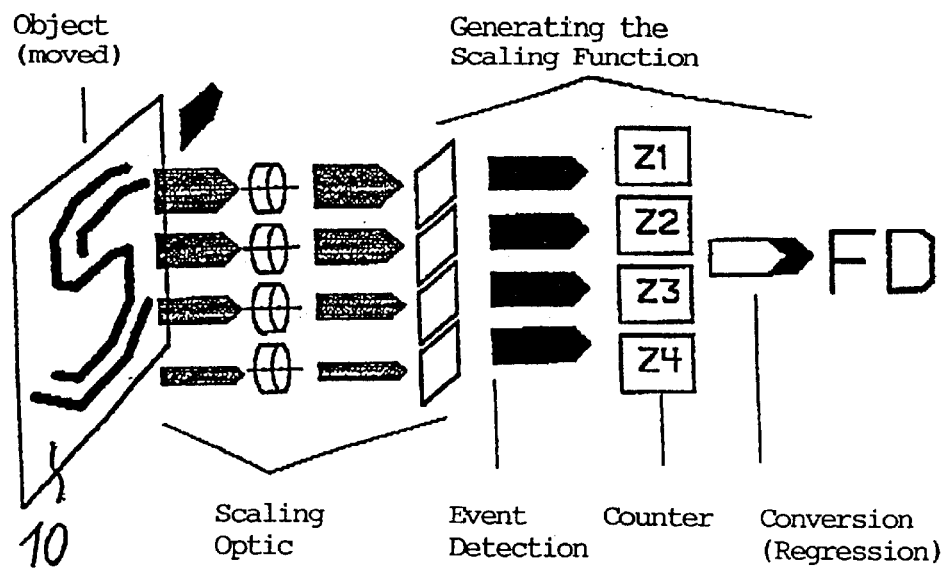

FIG. 17 shows a further representation in principle of the architecture of the method. A moving object 10 is illuminated and the imaging light bundle and/or the illumination ray bundle is scanned relative to the algorithm by way of a scaling optic as a sequence of light patterns. The connection of the light patterns and thus the detection of events is performed by way of the counters Z1, Z2, Z3, Z4, where the evaluation of the counters results in the fractal dimension FD.

A technical structure of a sensor for the sequential generation of light patterns for the illuminating of an object surface 10 is illustrated in FIGS. 4 through 7. The functional principle is a class formation of geometrical criteria by way of illuminating patterns on the object and, with respect to the object speed, a variation of the scanning frequency with an illuminating pattern with a simultaneous monitoring of the event noise on an event minimum. The illuminating patterns result from the combination of light pattern projection and illuminating time.

A sensor is illustrated in the two main sections through the optical axis 21. A socket 13 for an emitting and receiving element 14 is disposed within a casing 11 on a printed circuit board 12, wherein the emitting and receiving element 14 carries a tube 15, which is closed by way of a window and lens element 16. A multifocal illuminating imaging lens 17 is mounted below the window and lens element 16; the light bundling on the object 10 is performed by the combination of window and lens element 16 and illuminating imaging lens 17. The illuminating imaging lens 17 exhibits a central region 17' of a special lens structure for the focusing of the illuminating ray bundle 18, where the illuminating ray bundle 18 is surrounded by a region 17" of the special lens formation for the focusing of the converging ray bundle 19 on the two sides of 17', wherein the region 17" can also be provided torus-shaped around the region 17'.

The partial view of FIG. 6 C onto the emitter and receiving element 14 illustrates the geometrical arrangement of emitter and receiving faces of a semiconductor element of the emitter and receiving element 14. On the two sides of a series arrangement of emitter faces 14' on the horizontal center line there are two receiving faces 14" , 14'" disposed symmetrically on the vertical center line 22.

According to FIGS. 6 B and A the bundling of the light onto the object 10 is performed by way of a combination of optical elements or, respectively, optical regions 16' and 17' of the multifocal illuminating imaging lens 17, which for example in principle is a cylinder lens, constructed as holographic-optical element, within the region 17', which represents a spherical lens region with rectangular form of the width b (FIG. 6 A). Light reflected or, respectively, scattered by the object 10 is focused over the two lens sections 17" and 17'", disposed on the outside, onto the receiving faces 14", 14'" of the emitter and receiving element 14. FIG. 6 B shows the planar view onto the window and lens element 16, where the region 16' exhibits a rectangular form of the width b, such as the region 17' of the illuminating imaging lens 17, which region 16' is surrounded on the side by the side region 16", 16'". Structural data and speed determinations, the latter as a reference value for the first, are performed by way of the configuration of semi-conductor elements 14' and 14" and their optical coordination to the surface of the object 10 in an alternating mode of operation.

The illustration in FIG. 7 serves for the structural data determination by way of the example of the grid covering: A program-controlled grouping and activation of the emitter faces 14' generates in a time sequence a scale of illuminating faces 23 on the moved object 10, wherein the illuminating faces 23 are sequences according to the size, i.e. as smallest 23' of the length $S_{min}$ and as largest 23" of the length $S_{max}$, as well as based on time period duration. The size sequence and illuminating time are correlated thus that a conductor-shaped scanning grid 24 is placed over the object face 10, wherein the step width and number of the scanning grid 24 is iterated in a defined way. A class coordinated is synchronized on the receiving side with this illuminating program, for example by way of a partial covering of the respective grid face with the pattern.

A repeated, in each case position-staggered activation of an emitter-face configuration is performed on the emitter side for the speed determination, and in the simplest case of, for example only one emitter face. The image 25 thereof scans the object in the window region 26 with a resulting relative speed (from the scanning speed and the window region 26), in case of an emitter-side variation of the absolute scanning speed 27. The "event noise" assumes a minimum value with the directional and value equality of the speeds 20 and 27, signal flanks of events become flat in proximation to this state. This equality state is controlled in a suitable way on the evaluation side, for example by a feedback to the variation, and is detected: The relative speed of object surface to sensor is then determined from the known actual scanning speed 27.

The counting of the events over size classes of features is performed if desired with this device, wherein actual and known value of an illuminating face size on the emitter side controls filters on the evaluation side, for example time-window dimensioning for closed and finished events. Thus, the optical event noise of fracture faces of an investigation to scale invariance is also accessible, wherein it can be advantageous to separate the two receiving elements by forming classes.

A nesting serves for the size-dependent speed determination, wherein in addition, there is iteration over a group of various-sized emitter-face aggregates by way of the sensor control.

A sensor element of the above-described kind is set up with respect to dimensioning and operating data to applications with in each case the pattern to be expected. Line scanning and sequential illuminating program thus require corresponding scanning sizes in order to obtain reliable structural data; the pattern variations to be captured have to occur of course on a scanning track.

In principle, it is not necessary to be bound to the dimensional faithful imaging of emitter elements or to a rectangular structure of the illuminating pattern. Suitable adaptations can be performed by way of a transformation optic. Emitter and receiving elements can also be disposed, in a construction based on a transmitted light, on a joint optical axis (barrier construction) or as end faces of a light-conducting cable or of a light-conducting adapter part. The arrangement of one or several face elements is possible on the receiving side, wherein these face elements can generate in an integrating way one or several signals with in each case its own evaluation channel. The face elements can be disposed on the emitter side with different lengths ("length-scaled")

A further technical embodiment is illustrated in FIGS. 8 through 11. A drive motor 29 is disposed inside a casing 28, wherein the drive motor 29 drives a rotating hologram carrier 30, wherein the hologram carrier 30 exhibits two annular functional regions (FIG. 9), preferably in the shape of breakouts, i.e. an outer ring with illuminating program to the object and an inner ring for the synchronous evaluation control. At least one functional region serves for the generation of a scaled illuminating ray bundle and at least one functional region serves for the generation of a scaled imaging ray bundle. A photo barrier 31 serves for the scanning of the control value; a receiving diode 32 serves for receiving the scattered or, respectively, reflected light of the object 10. An illuminating ray bundle 33 is generated by way of a light source 37, for example a diode laser, which illuminating ray bundle 33 falls through an illuminating and collecting optics 34 onto the object 10 and is reflected or, respectively, scattered from there onto a light-divider mirror 35, wherein the light-divider mirror 35 guides the light onto the receiving diode 32. The aggregates are attached at a casing cover 36 of the casing 28 in a suitable way.

Figures 10, 11:
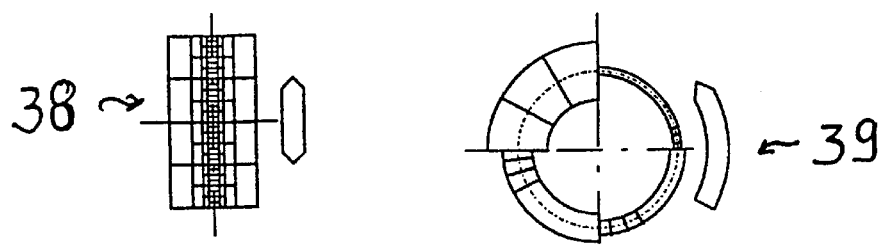

In case of a quasi non-moving object 10, the illuminating pattern is generated on the object surface by way of a rotating hologram of the hologram carrier 30 (for example, illuminating face variation and motion), wherein a linear illuminating pattern 38 is shown in FIG. 10, and wherein a circular illuminating pattern 39 is illustrated in FIG. 11. The control size for the signal evaluation referring thereto is synchronously read from the rotating hologram-carrier interior ring, which operates as an optical element.

Figure 12:
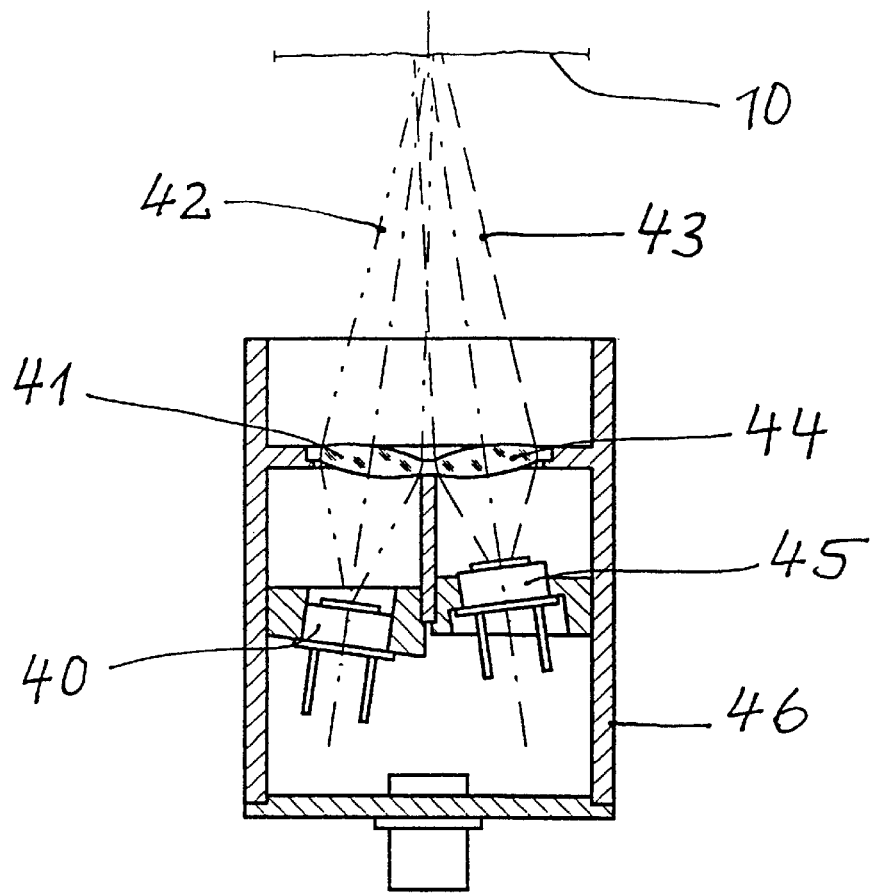

For the purpose of generating parallel illuminating patterns, wherein the aggregates of scaling scanning devices are employed in a series arrangement, FIG. 12 shows a construction variant with a schematic sectional representation cross to the row or sequence; the scanning motion is performed in this case perpendicular to the drawing face. A light-source array 40 with individually controllable emitter elements is disposed line-shaped within a casing 46, i.e. perpendicular to the drawing face. An illuminating ray path 42 in the form of light patterns is thrown onto the surface of an object 10 by way of an illuminating optic 41 and the illuminating ray path 42 is reflected or, respectively, scattered from there as an imaging or, respectively, receiving ray path 43, and is guided over an imaging-receiving optic 44 to receiving elements 45, wherein the receiving elements 45 are for example photodiodes, which are arranged line-shaped, i.e. perpendicular to the drawing face; the sensor is disposed in a casing 46. Advantageously, a parallel operation of the element pairs densifies the data capturing, wherein a mutual interference radiation is prevented by way of a spread light strip arrangement.

Figure 13:
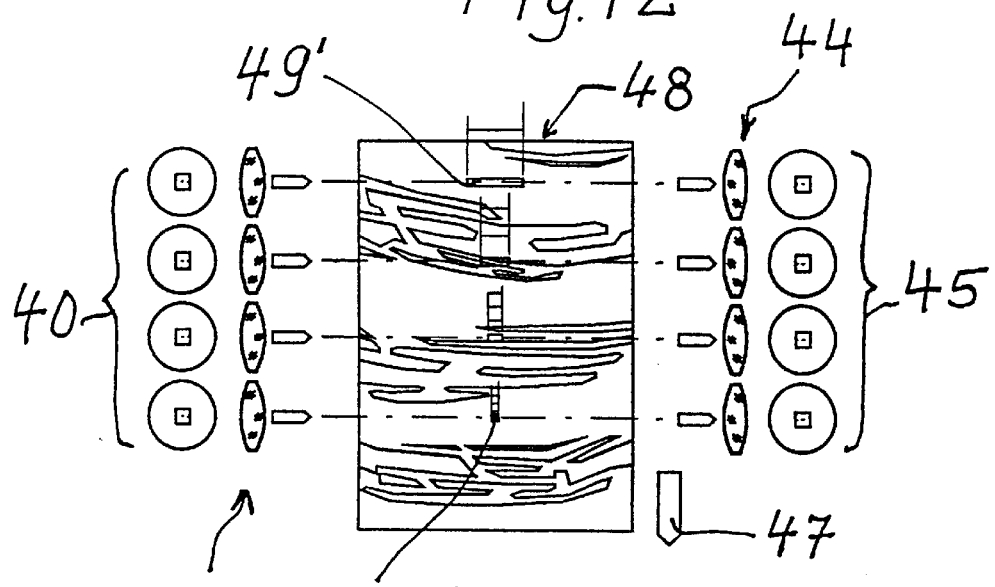

For this purpose, FIG. 13 schematizes the configuration of object 10, illuminating pattern, emitter and receiving elements 40, 45 in an unfolded representation. The object surface 10 with a strip pattern moves according to the directional arrow 47; the emitter elements of the light-source array 40 are disposed parallel thereto. A resulting illuminating pattern 48 is generated by horizontally arranged, strip-shaped light faces 49, 49' of a graduated length; the imaging or, respectively, receiving ray path 43 is guided over the sequence of the imaging-receiving optic 44 to the sequence of the receiving elements 45.

The optical structure for the purpose of an exact undistorted illumination and imaging is not illustrated in particular in the FIGS. 12 and 13, which can be achieved by way of diaphragms, aspherical components or forming of the emitter or, respectively receiving faces. The receiving optics cover in a sufficient amount in each case a light-strip contour 49, 49'. The sensor control of this example provides for the purpose of structural data detection that, in case of emitter-side constant light, there is performed a stepped charge integration on the receiving or, respectively, evaluation side, and in fact in constant relation to the object speed 47. The illuminating pattern 48 results in the example from four superposed, conductor-shaped individual grids of different dimension. The highest scanning frequency corresponds in this case to the smallest light strip 49.

Several illuminating patterns or, respectively, class-forming patterns are simultaneously applied in this structure onto an object, for example, a superposing grid, such as 48, combined with a window scale of stepped polarization directions, wherein in each case a polarizer and an analyzer can be disposed for this purpose on the emitter and receiving side. Similarly, this concept includes the combination of directional or color classes.

Object codings are performed with the combination of such object-close selective class formation and preconstructed patterns for this purpose, wherein the object codings are imitable or decipherable only with difficulty. A further variant provides that natural patterns are scanned with such a sensor configuration and the obtained structural data are documented on the pattern carrier.

Figure 14:
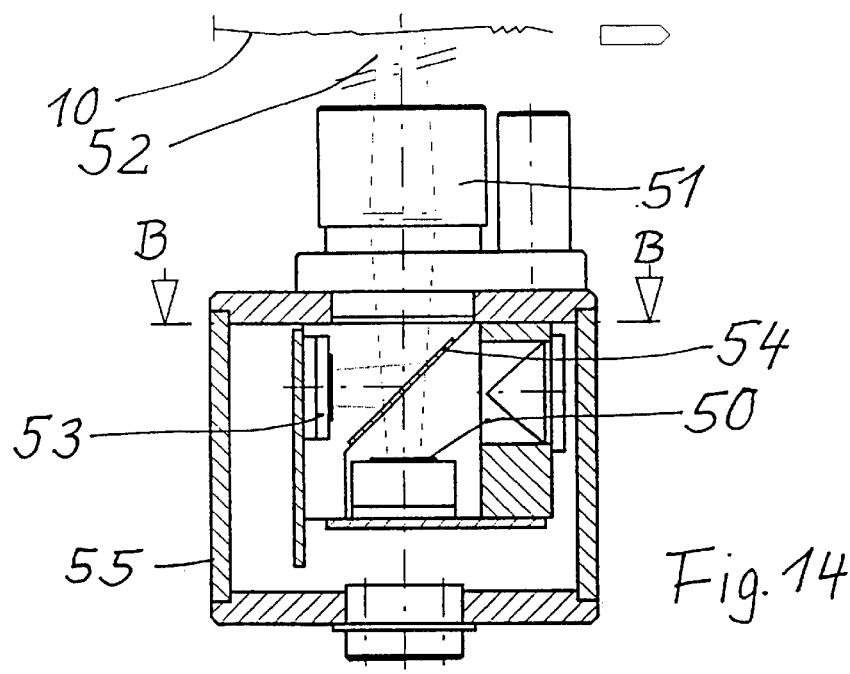
Figure 15:
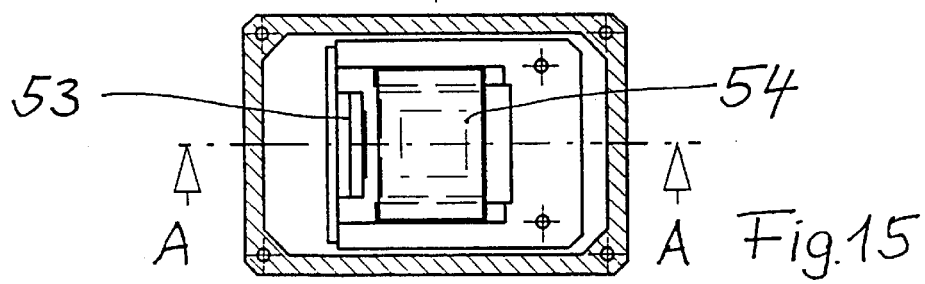

The sensor shown in the FIGS. 14 and 15 serves the face-covering scanning and has the purpose to provide a comparatively wider scanning track than it is realized with the described examples. The illuminating pattern is generated by grouping longitudinally scaled receiving elements in several parallel lines with again graduated integration times.

An emitter device element 50 with a matrix-shaped arrangement of emitter elements (FIG. 16*a*) is disposed inside a casing 55, wherein a variable-power objective of the zoom type 51, driven by a motor, has the purpose of the system adaptation to a certain size region (FIG. 16*b*), if necessary, by way of a step balancing. A light divider 54 is disposed within the illuminating and imaging ray path 52, wherein the light divider 54 deflects the imaging ray bundle to a receiving device element 53.

Figure 16:
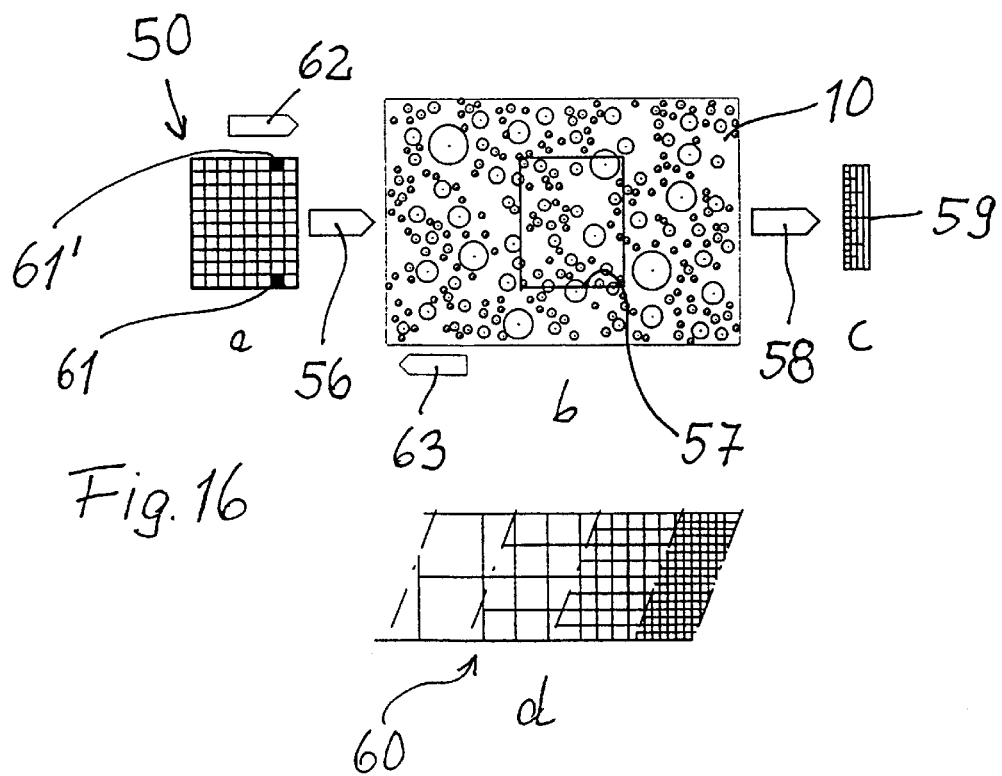

The light emitter face of the emitter device element 50 is subdivided in grid of individual emitter elements FIGS. 16*a* mainly for the purpose of the speed determination. In case of a non-uniform object speed in a pattern section 57, FIG. 16*b*, the activation of one or several emitter elements 61, 61' runs through several scanning tracks and thus delivers an effectively applicable speed. The totality of the receiving element 59 of the receiving-element array 59 is assumed as a receiving element. The motion of the illuminating configuration is rotated by 180 degrees with the illuminating optic 56 for the purpose of speed determination; the imaging ray path is guided to the receiving-element array 59, FIG. 16*c*, with the imaging optic 58. The resulting scanning grid 60 is shown in FIG. 16*d*. The motion of the illuminating configuration for the purpose of speed determination is designated by the reference numeral 63.

Sequential or spread generation of illuminating patterns prevents if required interfering overirradiation, the combination of several class-forming illuminating patterns expands the application to complex structures or as encrypting or encoding element in connection with preconstructed or natural structures. Amongst other things, a speed sensor is created thereby for moving material, which speed sensor can be adapted or, respectively set to certain structural features.

The contrasting of the features is performed by way of classical variations of the arrangement of the light impingement and scanning, of light or, respectively, dark field representation, of transmitted light or, respectively, reflected light. The contrasting of features critical for testing of a glazing in the reflected light, of shadow-forming pores in a side impinging light, of coated pills, preferably of the size of 1–4 mm, or of suspensions in the transmitted light occurs for example in this way. Test objects move relative to the sensor-scanning point with a constant speed in case of straight, circular, or zig-zag-shaped scanning track. This technique is well characterized as a "pattern-recognizing light barrier." The abstract criteria of the fractal dimension and the scaling function, which are primarily detected by the structure sensor, are interpreted depending on the application in a critical view respective to testing. The criteria concerned are such as constancy of the process, maintaining of tolerances, tendencies of development of criteria, class-similar appearing ensembles, homogeneity, uniformity of zones, demixing at edge zones, relative distribution of sizes.

The following possible applications of the structural sensor are recited for the food industry:

| Process | Criteria: |
|---|---|
| Comminution, separating | Totality, free of breakage or grinding |
| Crushing, grating | Relative size distribution, carving |
| Soaking, stirring | Dissolution of clumps or, respectively, fractions |
| Mixing | Distribution of components |
| Baking - cut face | Pores, grains |
| - surface | Scars, bubbles, glazing |
| Roasting, drying | Allowed structural variation, folding |
| Sorting | Ensembles of same appearance |
| Ripening | Surface variations |
| Fermenting | Development of bubbles, formation of spots |
| Coagulation | Phase transition, cluster, flocculation |
| Thickening - plates cubes | Surface variation depending on the object |
| Solidification by pressure | Homogeneity |
| Coating | Spots |
| Feeding of material | Presence of pests, spotty patterns and humidity |

Commercial Application

The invention is useful in particular for the detection of features of objects with dense, stochastically scattered arrangement of features, for example, at a continuous. Applications are in the food industry, in the technologies of medicine, environment, construction, sintering or energy. For example, granulates, such as grains, flakes, crystals, precipitants, ground material, crushed material, can be investigated relative to random arrangements typical for the material. Depending on the spectrum of size and form, specific weight, roughness, humidity, plasticity, elasticity, surface tension, gloss, color, and mixture, etc. there are present images of appearance which are dependent on process parameters such as pressure, temperature, or foreign components. In the solidified form these form material and process typical structures, which are in general modified by solidification process such as pressing, drying, baking, gluing, sintering, removal or addition of a component. The term granulate structure comprises also appearances which are not caused primarily from corn-shaped materials such as porous fields, bubble formation, fiber properties, waviness, and spot patterns.

List of the Reference Numerals

| | |
|---|---|
| 1, 2, 3, 4 | light pattern in the form of receiving elements |
| 5 | scaling controlled optical scanning of the imaging ray bundle |

-continued

| | |
|---|---|
| 6 | memory storage |
| 7 | scaling illumination of the illuminating ray bundle |
| 8 | scaling scanning of the imaging ray bundle |
| 9 | control |
| 10 | object surface |
| 11 | sensor housing |
| 12 | printed circuit board |
| 13 | socket for emitter and receiving element |
| 14 | emitter and receiving element |
| 14' | emitter faces of the emitter and receiving element |
| 14", 14''' | receiving faces of the emitter and receiving elements |
| 15 | tube |
| 16 | window and lens element |
| 16', 16", 16''' | region of the window and lens elements |
| 17 | multifocal illumination imaging lens |
| 17' | region of the special lens structure for focusing the illuminating ray bundle |
| 17", 17''' | externally disposed region of the special lens structure for focusing the light-capturing bundle on both sides of the region 17' |
| 18 | illuminating ray bundle represented in its smallest extension and in central position |
| 19 | converging ray bundle on both sides of the region 17' |
| 20 | direction of the relative motion between object and illumination focus |
| 21 | optical axis |
| 22 | vertical center line |
| 23 | illuminating faces |
| 23', 23" | smallest and largest illuminating faces |
| 24 | conductor-shaped scanning grid |
| 25 | image of the emitter face 14' |
| 26 | window region |
| 27 | absolute scanning speed |
| 28 | casing |
| 29 | drive motor |
| 30 | rotating hologram carrier with two circular-shaped functional regions |
| 31 | photo barrier for scanning the control value |
| 32 | receiving diode for scattered or, respectively, reflected light of the object |
| 33 | illumination bundle |
| 34 | illumination and collecting optic |
| 35 | light-divider mirror |
| 36 | casing cover with attachment of the individual elements |
| 37 | light source, for example diode laser |
| 38 | example of a linear illuminating pattern |
| 39 | example of a circular illuminating pattern |
| 40 | light-source array with individually controllable emitter elements, disposed line-shaped (perpendicular to the drawing face) |
| 41 | illuminating optic |
| 42 | illuminating ray path |
| 43 | imaging or, respectively, receiving ray path |
| 44 | imaging receiving optic |
| 45 | receiving elements, for example photodiodes disposed line-shaped (perpendicular to the drawing face) |
| 46 | casing |
| 47 | directional arrow |
| 48 | resulting illuminating pattern |
| 49, 49' | strip-shaped light faces of graduated length |
| 50 | emitter device element with matrix-shaped disposition of emitter elements |
| 51 | variable-power objective of the zoom type, driven by a motor |
| 52 | illuminating and imaging ray path |
| 53 | receiving device element |
| 54 | light divider |
| 55 | casing |
| 56 | illuminating optic |
| 57 | pattern section |
| 58 | imaging optic |
| 59 | receiving-element array |
| 60 | resulting scanning grid |
| 61, 61' | emitter-element configuration for the speed determination |
| 62 | motion arrow |
| 63 | motion of the illumination configuration for speed determination |

What is claimed is:

1. A method for an optical detection of object streams, wherein surfaces of the moving object streams are capable of reflecting or scattering light, and wherein the object streams are capable of providing self-similar patterns or structures on the surfaces of the object streams comprising: employing an illuminating device for illuminating the object streams capable of reflecting and scattering light;

generating patterns derived from the surfaces of the object streams when the surfaces of the object streams are illuminated by the illuminating device;

scanning an imaging ray bundle reflected from the surfaces of the object streams and scattered by the object streams based on a similitude-transformation algorithm wherein the scanning is performed by an optical imaging and receiving device and wherein a result of the scanning is a sequence of imaging light patterns, and wherein a connection of individual light patterns to each other is at least one of spatially and timely and is a self-similar transformation of individual light patterns;

setting up at least two variables; storing of detection events, resulting from the scanning over variables, in a form of value pairs, performed within a memory storage in an affine transformation;

calculating a self-similar transformation function performed by way of a logarithm of the at least two variables of the self-similar transformation.

2. The method according to claim 1, further comprising:

modulating an illumination ray bundle with a sequence of light patterns illuminating the objects, wherein the similitude-transformation algorithm forms the basis of the modulating, wherein the modulating of the illuminating ray bundle, the scanning of the imaging ray bundle, and a control of the memory storage for receiving the value pairs are tuned to each other in a controlled way by means of a control circuit.

3. The method according to claim 2, wherein during at least one of the scanning of the imaging ray bundle and the modulating of the illuminating ray bundle, the light patterns are scaled and comprise a group of illuminating faces, which group of illuminating faces form a scaling of exactly self-similar light patterns in a plane with respect to at least one common property if an exactly self-similar pattern is to be recognized as a constant.

4. The method according to claim 1, wherein the object stream is a resting object, and wherein the light patterns comprise a sequence of size-sequenced rectangles.

5. The method according to claim 1, wherein the object stream is a moving object stream, and wherein the light patterns comprise length-sequenced lines.

6. The method according to claim 1, wherein the light patterns are nested in light pattern sections, wherein scaling properties of the light patterns are maintained during the nesting.

7. The method according to claim 6, wherein a nested variation serves for a size-dependent determination of speed, wherein there is iterated in addition over a group of differently sized emitter face aggregates by way of a control circuit.

8. The method according to claim 1, wherein the light patterns are scanned and varied, respectively, with respect to one or several scaling parameters.

9. The method according to claim 8, wherein
a parallel size variation of all surfaces to be illuminated is performed periodically for the scanning and variation, respectively, of the scaling parameters.

10. The method according to claim 1, wherein
the self-similarity of the light pattern is scanned and varied, respectively, from self-affine over exactly self-similar to fractal.

11. The method according to claim 10, wherein
the scanning and variation, respectively, of the self-similarity of the light pattern is performed by way of a non-linear, image-distorting variable-power objective of the zoom type.

12. The method according to claim 11, wherein
the imaging and receiving side are structured such that one or several scaling parameters are mutually coordinated in a channel-forming way in a scaling over degrees of a member selected from the group consisting of polarization scale and a decolorization scale in connection with an optical superpositioning of a member selected from the group consisting of light pattern elements, object features and combinations thereof.

13. The method according to claim 1 wherein a determination of an average value is performed continuously over the value pairs with each new value of the scanning.

14. The method according to claim 1, wherein
the variables of the affine transformation are a member selected from the group consisting of size-sequenced polygons, time-sequenced polygons, squares, rectangles, lines, angles, colors, degrees of polarization, electromagnetic wave length, acoustic wave lengths.

15. An apparatus for an optical detection of resting objects or moving object streams, wherein surfaces of the resting objects or moving object streams are capable of reflecting or of scattering light, and wherein the resting objects or moving object streams can exhibit self-similar patterns or structures on the surfaces, with an illuminating device for illuminating the objects or object streams and an optical imaging and receiving device with a sequentially following electronic evaluation for receiving and evaluating an imaging light reflected or scattered by the surfaces, characterized by the following features:
a) an optical device which is capable of scanning an imaging ray bundle as a sequence of light patterns, wherein a similitude-transformation algorithm forms a basis of the scanning such that a connection of individual light patterns relative to each other spatially and/or timely is a scaling or rotation or translation of self-similar, and wherein at least two variables are set up,
b) a storing of detection events, resulting from the scanning over the variables, in a form of value pairs, is performed within a memory storage of the scaling or rotation or translation,
c) a calculation of the scaling or rotation or translation functions is performed by way of a logarithm of the variables of the scaling or rotation or translation.

16. The apparatus according to claim 15 further comprising
a further optical device in front of the object or object stream, wherein the further optical device is also capable of modulating the imaging ray bundle with a sequence of light patterns, wherein in a similar way a similitude-transformation algorithm forms a base of the modulating such that the connection of the individual light patterns relative to each other spatially and/or timely is a scaling or rotation or translation of self-similar, and wherein at least two variables are set up, and furthermore a control device, which is connected to the two optical devices in a controlling way, wherein the modulating of an illuminating ray bundle, the scanning of the imaging ray bundle, as well as a control of the memory storage are tuned to each other for receiving the value pairs.

17. The apparatus according to claim 15 wherein
the optical device comprises an emitter and receiving element, where a window and lens element follows to the emitter and receiving element, wherein an illuminating imaging lens is disposed below the window and lens element in a direction to the object, wherein the light bundling onto the object is performed in combination by way of the window and lens element and the illuminating imaging lens.

18. Apparatus according to claim 17, characterized in that the illuminating imaging lens exhibits a central region of a lens structure for focusing an illuminating ray bundle, which is surrounded on two sides by outer disposed regions for focusing a light-capturing bundle on two sides of the central region.

19. The apparatus according to claim 15 further comprising
a motor-driven rotating hologram carrier serving for generating the sequence of light patterns according to a given scaling, wherein the hologram carrier exhibits at least two functional regions, in particular as preset breakouts, and wherein the hologram carrier can be illuminated with a light source for generating an illuminating face variation and illuminating face motion, wherein the functional regions are disposed linearly or circularly, wherein at least one functional region serves for generating a scaled illuminating ray bundle and at least one functional region serves for generating a scaled imaging ray bundle.

* * * * *